United States Patent [19]

Tammisalo

[11] 4,449,225
[45] May 15, 1984

[54] METHOD TO BE USED IN PANORAMIC X-RAY PHOTOGRAPHY AND AN APPARATUS FOR CARRYING OUT THE METHOD

[76] Inventor: Erkki Tammisalo, Linnunpäätie 3, SF-20840, Turku 84, Finland

[21] Appl. No.: 348,996

[22] Filed: Feb. 16, 1982

[30] Foreign Application Priority Data

Feb. 20, 1981 [FI] Finland .................................. 810530

[51] Int. Cl.³ .............................................. G03B 41/16
[52] U.S. Cl. ........................................ 378/39; 378/91
[58] Field of Search .................................. 378/39, 40

[56] References Cited

U.S. PATENT DOCUMENTS 4,340,971 7/1982 Furuichi ................................ 378/40

*Primary Examiner*—Craig E. Church
*Attorney, Agent, or Firm*—Bucknam and Archer

[57] ABSTRACT

The invention relates to carrying out a pre-adjustment, before photographing is started, in panoramic X-ray photography using an X-ray device which performs a rotational movement and supports a moving film and an X-ray source. The object is to achieve a correct positioning of the focus in relation to the patient. This is achieved without moving either the patient or the X-ray apparatus, or more precisely, merely by selecting the correct ratio between the film speed and the movement of the X-ray apparatus, instead of mechanical movement. In the apparatus, a viewing member is used, and the correct speed variation curve for the film during the photographing movement is selected on the basis of the position or reading of the viewing member. The film is reeled preferably by means of an electric motor, in which case a sensor can be connected to the sighting member, and the motor is controlled electronically according to the electric output signal of the sensor by means of, for example, a microprocessor.

5 Claims, 2 Drawing Figures

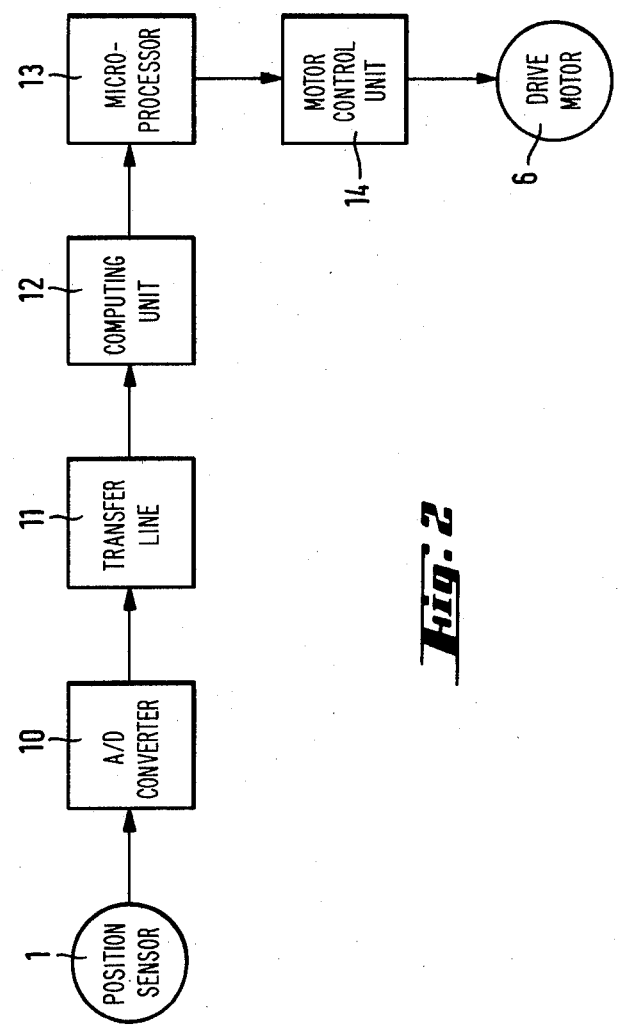

METHOD TO BE USED IN PANORAMIC X-RAY PHOTOGRAPHY AND AN APPARATUS FOR CARRYING OUT THE METHOD

BACKGROUND OF THE INVENTION

1. Field of the Invention

The present invention relates to an improved method to be used in panoramic X-ray photography by means of an X-ray device which performs a rotational movement and comprises an X-ray source and a moving film, for adjusting the areas of focus to the correct point in relation to the patient before photographing is started, a method in which the patient is supported by means of support members and, for the purpose of adjustment, a viewing member is moved to the correct point in relation to the patient. The invention also relates to an apparatus for carrying out this method. The invention relates in particular to panoramic tomography, i.e. photography of a patient's denture, but it can also be applied to other cases of X-ray photography in which an X-ray source and a film, situated on different sides of the patient, are rotated around the patient during the photographing, while the film is reeled forwards.

2. Description of the Prior Art

It is known that the shape of the layer which is photographed with precision can be affected by means of the geometry of the X-ray apparatus, and, especially in panoramic tomography apparatus, by making arrangements for a combined linear and rotational movement of the support arm which suports the X-ray source and the film cassette at its opposite ends.

In order to bring the patient and the apparatus to the correct position in relation to each other before photographing is started, it has been known to use a viewing device indicating the object to be photographed and to move the patient to the correct point by means of this viewing device. The disadvantages of this method are the structural requirements set by it on the patient-supporting members and the moving of the patient after the initial setting, resulting in the lengthening of the time used for the photographing and sometimes also in an imprecise X-ray photograph.

Another alternative suggested in order to avoid moving the patient is to connect the suspending part of the support arm of the X-ray device mechanically to the viewing device, in which case the patient is always placed in the same position by means of stationary support members, and the fine adjustment is carried out by moving the X-ray, apparatus itself. The disadvantage of this alternative is its structurally complicated and expensive moving mechanism, as we must remember that, after the initial setting, the X-ray device, in other words, the support arm, further performs the said combined linear and rotational movement.

Furthermore, in panoramic X-ray photography the speed of the film is controlled in such a manner that at each given moment it corresponds to the speed of the point being photographed, as the point is taken as projected onto the film surface.

SUMMARY OF THE INVENTION

It is an object of the present invention to eliminate the above-mentioned disadvantages of known apparatus in such a manner that the patient can also be placed in a stationary position by means of the support members of the apparatus, and that the moving part of the X-ray device, for example, the support arm, can also perform the same movement without fine adjustment of the initial point before photographing is started. This objective is achieved by taking advantage of the effect of the film speed in relation to the object being photographed. By means of different adjustments of the film speed it is, namely, possible to move the position of the object being photographed, e.g. a denture, without moving the patient or the X-ray device. Accordingly, the present invention provides an improved method of the character once described, wherein the improvement comprises maintaining the support members and the suspending point of the X-ray device in a stationary position in relation to each other and performing the pre-adjustment of the area of focus by affecting, on the basis of the position therefore or reading of the sighting member, the ratio between the film speed and the movement of the X-ray device. The invention also provides an apparatus for carrying out this method, said apparatus comprising a stationary frame;
an X-ray device provided on the frame and having a suspending part for enabling a combined linear and rotational movement of the X-ray device;
an X-ray source and a film holder with film-reeling means provided on the X-ray device;
patient supporting members;
a sighting member to be aimed at a predetermined point in the patient;
both the patient supporting members and the suspending part of the X-ray device being stationary in relation to the frame, and
the ratio between the speed of the film reeling member and the X-ray device being controlled on the basis of the position of the sighting member.

The invention and its other characteristics are described below in greater detail in the form of an example and with reference to the accompanying drawings.

BREIF DESCRIPTION OF THE DRAWINGS

FIG. 1 is a diagrammatic representation of a side elevation of an X-ray apparatus intended for photographing a denture, and FIG. 2 is a block diagram of the circuitry of the apparatus according to the invention.

DESCRIPTION OF THE PREFERRED EMBODIMENTS

Figure 1:
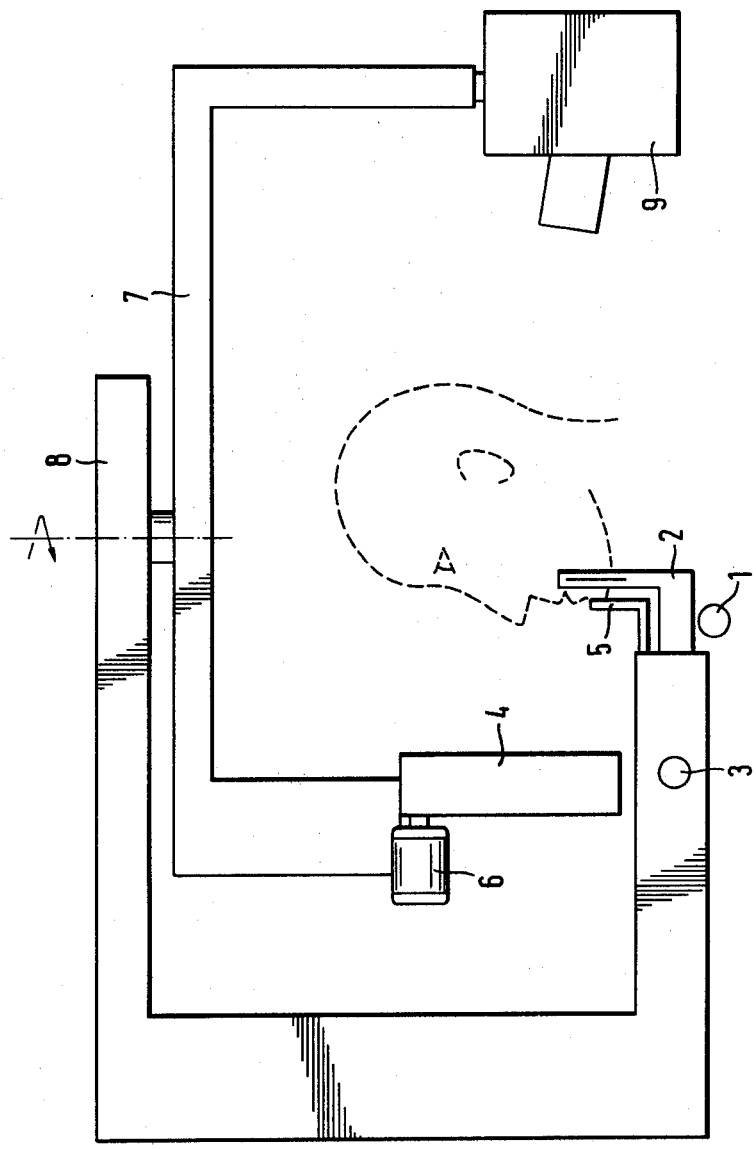

The apparatus depicted in FIG. 1 includes the following parts: A position sensor 1, a viewing member 2 indicating the layer being photographed, a moving mechanism 3 for the sighting member, an image registration apparatus 4 consisting of a moving film cassette, a patient support 5 which is stationary in relation to the supporting frame, a drive motor 6 for the image registration device, a rotating support arm 7, a supporting frame 8, and an X-ray source 9. The support 5 can, of course, be replaceable depending on the object which is being photographed at a given time.

In this X-ray apparatus the support arm 7 with its X-ray source 9 and film 4 thus rotates during the photographing around the patient's head according to a predetermined geometry. Since, as regards this part, the apparatus is completely known for an expert in the art, reference is made here as regards its operation only by way of example to previous Finnish Patent Application No. 763569.

That which is essential in the present invention is that the patient is always placed in a stationary position with the aid of supporting member 5, and that the moving mechanism 3 for the sighting member does not affect the position of the support arm itself but only the control of the drive motor 6, preferably electronically.

In FIG. 2, the block diagram of the circuitry is depicted in greater detail. It thus includes a position sensor 1 connected to the viewing member, a converter 10, which can be an analog/digital converter or, for example, a voltage/frequency converter, a transfer line 11, a computing unit 12, a microprocessor 13, and a motor control unit 14.

The output of the position sensor 1, which thus indicates the place of the indicator device adjusted to the correct position in relation to the patient, can be, for example, an analog voltage signal, as is well known in the art of control techniques and electronics. This signal is converted in the converter 10 either to a corresponding digital signal or to a frequency signal, the frequency of which corresponds to the position of the indicator. The transfer line 11, which can be a suitable cable, transfers the converter output signal to the computing unit 12, which operates in conjunction with the microprocessor. The control programs for the drive motor 6 have been programmed into the microprocessor, and the programs are selected on the basis of the data obtained from the computing unit 12, i.e. on the basis of the actual position of the object being photographed. The processor can, of course, have fixed circuitry or be freely programmable. The motor 6 can be a step motor into which the motor control unit 14 feeds control pulses at a varying frequency controlled by the microprocessor 13. It is, of course, also possible to use as the drive motor a DC motor controlled by means of a varying voltage.

In currently used X-ray apparatus, mechanical transmission which changes according to the movement of the support arm is generally used for the control of the film speed. It is evident that such mechanical transmission can also be applied to the present invention in such a manner that the initial setting of the trnsmission ratio is carried out on the basis of the reading of the position sensor.

What is claimed is:

1. In a method to be used in panoramic X-ray photography for adjusting the shape of the layer which is photographed with precision to the correct point in relation to the patient before photographing is started, and of the type wherein an X-ray device performs a rotational movement and comprises an X-ray source and a moving film, and wherein the patient is supported by means of support members and, for the purpose of adjustment, a viewing member is moved to the correct point in relation to the patient, the improvement comprising maintaining the support members and the suspending point of the X-ray device in a stationary position in relation to each other and performing the pre-adjustment of the shape of the layer which is photographed with precision by preselecting, on the basis of the position or reading of the viewing member, the film speed.

2. A method according to claim 1, wherein an electric motor which reels the film is controlled by means of a microprocessor to which control signals are fed, said signals being dependent on the position or reading of the viewing member.

3. An apparatus for carrying out panoramic X-ray photography, said apparatus comprising:
    a stationary frame;
    an X-ray device provided on the frame and having a suspending part for enabling a combined linear and rotational movement of the X-ray device, said X-ray device comprising
    an X-ray source and a film holder with film-reeling means;
    patient supporting members;
    a viewing member to be aimed at a predetermined point in the patient;
    means connected to said viewing member and functioning to preselect the film speed in response to a signal from said viewing member while both the patient supporting members and the suspending part of the X-ray device remain stationary in relation to the frame.

4. An apparatus according to claim 3, wherein the film-reeling member is an electric motor which is controlled by said means connected to said viewing member which comprises an electronic circuit, the electronic circuit having a control input to which said signal corresponding to the position or reading of the viewing member is supplied.

5. An apparatus according to claim 4, wherein the electronic circuit includes a microprocessor in which certain control programs for said electric motor have been programmed, the parameter of the program being derived from the position or reading of the viewing member.

* * * * *